United States Patent [19]

Soudant et al.

[11] Patent Number: 5,728,393
[45] Date of Patent: Mar. 17, 1998

[54] PROCESS FOR COMBATING ADIPOSITY AND COMPOSITIONS WHICH MAY BE USED FOR THIS PURPOSE

[75] Inventors: Etienne Soudant, Fresnes; Jean-Francois Nadaud, Clamart, both of France

[73] Assignee: L'Oreal, Paris, France

[21] Appl. No.: 661,762

[22] Filed: Jun. 11, 1996

Related U.S. Application Data

[63] Continuation of Ser. No. 347,076, Nov. 23, 1994, abandoned.

[30] Foreign Application Priority Data

Nov. 26, 1993 [FR] France ................... 93 14156

[51] Int. Cl.⁶ ........................................ A61K 7/48
[52] U.S. Cl. ...................... 424/401; 514/25; 514/27; 514/45; 514/547
[58] Field of Search ..................... 424/401; 514/45, 514/25, 27, 579, 909, 547

[56] References Cited

U.S. PATENT DOCUMENTS

| | | | |
|---|---|---|---|
| 4,042,687 | 8/1977 | Gans | 424/177 |
| 4,288,433 | 9/1981 | Koulbanis | 424/232 |
| 4,588,724 | 5/1986 | Greenway | 514/250 |
| 4,920,016 | 4/1990 | Allen | 424/450 |
| 5,055,460 | 10/1991 | Friedlander | 514/161 |
| 5,211,956 | 5/1993 | Sawai | 424/451 |
| 5,369,030 | 11/1994 | Hannun | 435/240.2 |
| 5,376,371 | 12/1994 | Bombardelli | 424/195.1 |

FOREIGN PATENT DOCUMENTS

| | | |
|---|---|---|
| A-0371844 | 6/1990 | European Pat. Off. |
| A-0493151 | 7/1992 | European Pat. Off. |
| A-2273514 | 1/1976 | France |
| A-2369840 | 6/1978 | France |
| A-2679770 | 2/1993 | France |
| WO-A-9211838 | 7/1992 | WIPO |

OTHER PUBLICATIONS

Patent Abstracts of Japan, vol. 8, No. 134 (C–230) (1571) 21 Jun. 1984 of JP 59 044 313.

*Primary Examiner*—Gollamudi S. Kishore
*Attorney, Agent, or Firm*—Oblon, Spivak, McClelland, Maier & Neustadt, P.C.

[57] ABSTRACT

The invention relates to a treatment and/or prevention of the problems of adiposity, with the aim being to obtain a cosmetic and/or therapeutic slimming effect which is generalized or localized on the human or animal body, the said process being characterized in that it consists in administering to the body, preferably via the topical route, at least one substance capable of limiting or of inhibiting the uptake of glucose by adipocytes. In addition, it is also possible to supply the body, preferably via the topical route, with at least one compound capable of stimulating lipolysis, the said supply being made in a simultaneous or separate manner or spread out over time relative to the step for administration of the glucose-uptake inhibitors. It also relate to various cosmetic, dermatological and/or medicinal compositions intended for implementation of the said process, as well as to their various uses.

4 Claims, No Drawings

PROCESS FOR COMBATING ADIPOSITY AND COMPOSITIONS WHICH MAY BE USED FOR THIS PURPOSE

This application is a continuation of application Ser. No. 08/347,076, filed on Nov. 23, 1994, now abandoned.

FIELD OF THE INVENTION

The present invention relates to a treatment and/or prevention process aimed more particularly at decreasing or combating the problems of adiposity, with the aim being in particular to obtain a cosmetic and/or therapeutic slimming effect which is generalized or localized on the human or animal body.

It also relate to various cosmetic, dermatological and/or medicinal compositions intended in particular for implementation of the said process, as well as to their various uses.

BACKGROUND OF THE INVENTION

Adiposity (or excess fat in the subcutaneous cellular tissue) may have many causes, of varying complexity, and the understanding of which also varies greatly.

Some skin cells, known as adipocytes, contain variable amounts of fats in the form of triglycerides, which are synthesized in vivo via enzymatic reactions (lipogenesis), starting from free fatty acids and glycerol contained in the body and supplied to it via certain foods. Glycerol is obtained in vivo, by degradation of glucose. Now, in parallel, the triglycerides stored in the adipocyte cells may also be redegraded, under the action of specific lipolytic enzymes contained in these same cells. Redegradation liberates fatty acids, on the one hand, and glycerol and/or glycerol mono- and/or diesters, on the other hand. The fatty acids may then either diffuse in the body to be consumed or converted therein in different ways, or be taken up again (immediately or slightly later) by the adipocytes to again generate triglycerides by lipogenesis.

For various reasons (i.e. excessively rich food, inactivity, ageing and others), a substantial imbalance is established in the body between lipogenesis (i.e. the formation of triglycerides by enzymatic reaction between fatty acids and glycerol obtained from glucose) and lipolysis (i.e. the enzymatic decomposition of triglycerides into fatty acids and glycerol). Accordingly, if the amount of fatty substances formed by lipogenesis become appreciably and consistently greater than those which are eliminated by lipolysis, an accumulation of triglycerides occurs in the adipocytes. If this becomes excessive, it may be progressively reflected in the appearance of a thick skin with an often irregular surface ("orange-like skin") of a consistency which is flaccid or gelatinous to a greater or lesser extent. The final result is figure with an unattractive general appearance which may progress from the simple local excess (lipodismorphy), passing through a certain stoutness, and finally genuine obesity.

In view of the profound discomfort, both physical and aesthetic, and sometimes psychological, which it often causes in individuals suffering from it, in particular in women, adiposity nowadays constitutes a condition which is less and less well tolerated or accepted.

Methods have been proposed to treat adiposity, however, only the surgical methods, such as liposuction, currently provide truly satisfactory results. However, liposuction has the major drawback of being an invasive operation, which is intricate, not without risk and often expensive.

Accordingly, there is a strong need for a "mild" cosmetic and/or non-surgical therapeutic treatment which effectively combats against human or animal adiposity. In particular, there is a need to obtain a general or, on the contrary, localized effect of slimming and/or thinning of the skin or of the figure.

The present invention is aimed precisely at satisfying such a need.

Thus, after considerable research conducted in this matter analysis and interpretation of the multiple causes, factors and mechanisms, partly known per se, associated with adiposity, it has now been found, quite unexpectedly and surprisingly, that the above objective is achieved using a novel treatment process, which consists essentially of limiting, or in totally inhibiting the glucose uptake by the adipocyte cells, contained in the skin. Thus, by limiting or by preventing the diffusion of extracellular glucose into adipocytes (which "exhausts" the source of glycerol, essential for the storage of fats), it is possible to substantially decrease, the formation of the triglycerides in adipocytes which are normally generated by lipogenesis from the free fatty acids originating either from the diet or from lipolysis itself. It has been found that the desired technical effect could be obtained, by supplying the body, in particular the skin cells, with certain specific non-cytotoxic substances capable of effectively inhibiting glucose uptake by the adipocytes. Finally, it has been found that their effects can be further reinforced when glucose-uptake inhibitors are administered in conjunction with at least one compound capable of stimulating or activating lipolysis. Such a combination has been found to synergistically inhibit triglyceride formation.

All these discoveries form the basis of the present invention.

SUMMARY OF THE INVENTION

Thus, according to a first aspect of the present invention is a non-therapeutic in vivo treatment to combat adiposity and thus to obtain a slimming effect on the skin, the said process comprising administering to the body, via the topical and/or systemic route, at least one substance, without sulfur, capable of limiting or of inhibiting the uptake of glucose by adipocytes.

A second embodiment of the treatment process further comprises administering to the body, at least one compound capable of stimulating lipolysis. The lipolysis stimulating compound may be via the topical and/or systemic route. The lipolysis stimulating compound may be administered concurrently, separately or alternatively spread out over time, relative to administration of the glucose-uptake inhibitor.

According to a third aspect of the present invention, a cosmetic and/or therapeutic composition is provided suitable for implementation of the above treatment process taken in its diverse variants, topical route, systemic route, use or otherwise of a lipolysis stimulator, said compositions comprising i) at least one substance, without sulfur, capable of limiting or of inhibiting glucose uptake by adipocytes, ii) at least one compound capable of stimulating lipolysis; and iii) a physiologically acceptable carrier which is compatible with the chosen mode of administration, According to a fourth aspect of the present invention, a device containing several compartments or "a kit" for implementation of the above process is also provided. The device comprises, in a first compartment, one or more glucose-uptake inhibitors and, in a second compartment, one or more lipolysis stimulators, the compositions contained in the first and second compartments being considered here as combination compositions, for simultaneous or separate use or for use spread out over time, in a treatment intended to combat adiposity and/or to obtain a slimming effect.

Finally, another subject of the invention is the use of one or more substances, without sulfur, capable of limiting or of inhibiting glucose uptake by adipocytes as active principles in, or for the production of, cosmetic or therapeutic compositions intended to combat adiposity and/or to obtain a local or global slimming effect on all or part of the body, whether human or animal.

DETAILED DESCRIPTION OF THE PREFERRED EMBODIMENTS

Within the context of the present invention topical administration is understood to refer to any technique for administration of a product by direct application of the latter to a surface (or external) part of the body, such as the skin, and systemic administration is understood to refer to any technique for administration of a product via a route other than topical, for example oral and/or parenteral.

Likewise, in that which follows, "glucose uptake inhibitor" is understood more simply to denote any substance which makes it possible, in vivo, to limit or to inhibit totally the mechanisms of glucose uptake and transport in adipose cells (adipocytes). In particular, "glucose uptake inhibitors" inhibit the mechanisms associated with the activity of at least one of the two glucose transporters known under the name GLUT-1 (erythrocyte/brain-type) and GLUT-4 (muscle/adipose-type) present in adipocytes. The inhibitory nature, or the absence of inhibitory nature, of a given substance with respect to glucose uptake by the adipocytes may be determined by a person skilled in the art, by conventional methods such as using the biochemical test outlined below in the examples. According to the present invention, inhibitors which act more specifically or selectively on GLUT-4 are preferably used, because there glucose transporters are insulin-independent, which eliminates any risk of interference with the physiological regulation of glycemia.

Within the context of the present invention, the glucose-uptake inhibitor is "without sulfur", meaning, that the glucose-uptake inhibitor does not contain the element of sulfur, either in molecular or radical form.

Finally, a lipolysis "stimulator" is understood to refer to any substance which, in vivo, makes it possible to, directly or indirectly, stimulate lipolytic activity in the adipocytes. Such agents with lipolytic activity, as well as the various mechanisms of action associated with them, are already well known per se, and among these there may more particularly be mentioned xanthic bases (i.e. xanthine derivatives), such as theophylline, caffeine, theobromine and 1-hydroxyalkylxanthines and their compatible salts (see in particular on this subject document FR-A-2 617 401), nicotinic acid derivatives, more particularly such as alpha-tocopherol nicotinate and hexyl nicotinate (see in particular on this subject document EP-A-371 844), substances known as alpha-2 blockers which are capable of blocking the alpha-2 receptors at the surface of adipocytes, for example such as ginkgo biloba (see in particular on this subject document FR-A-2 669 537), and finally growth factors (see in particular on this subject document FR-A-2 671 487), it being possible, of course, within the context of the present invention, for all these compounds to be used alone or as mixtures.

According to a preferred embodiment of the present invention, the glucose-uptake inhibitor is selected from the group consisting of serine, rutine, ceramides, N-oleyldihydrosphingosine and a mixture thereof. N-oleyldihydrosphingosine is preferred. These products have proved to be particularly effective in the process according to the invention for decreasing the content of fats in the skin. The first two amino acids mentioned may be used as they are or in the form of their corresponding polymers (peptides). Moreover, these inhibitors may be supplied in the form of natural products containing them, or alternatively in the form of synthetic products, when this is possible.

The glucose-uptake inhibitors are preferably supplied to the body via the topical route. In this way, it is possible to obtain the desired slimming effect in a localized manner and with control (selectivity) as regards to the various parts of the skin which it is more specifically desired to treat. In contrast, systemic administration results in a slimming effect obtained over the whole body. In the case of systemic administration, oral administration if preferred.

The same administration considerations apply to the lipolysis stimulators, when these compounds are used in combination or separate manner or spread out over time, with the glucose-uptake inhibitors, that is to say that they are also preferably administered via the topical route.

Thus, in general, the glucose-uptake inhibitors, as well as the optional lipolysis stimulators, used within the context of the present invention may be packaged in a conventional manner in a suitable form for the mode of administration or of application finally chosen for the latter (lotions, emulsions, gels, creams, tablets, gelatin capsules, sugar-coated pills, wafer capsules, syrups and others). The compositions more particularly targeted by the present invention are thus compositions of cosmetic and/or pharmaceutical type containing, in a physiologically acceptable carrier, at least one glucose-uptake inhibitor as active principle, in combination optionally with at least one lipolysis stimulator. The compositions are preferably formulated and packaged in a form adapted to an application via the topical route. Alternatively packaging is in a form adapted to an administration via the systemic route, advantageously the oral route.

The same considerations apply to the case of the "kits" in accordance with the invention; in particular, the compositions included in each of the compartments of the kit are preferably formulated in a suitable form for a topical application. In this regard, it will be noted that, according to the present invention, it is possible to design presentation kits containing as many separate compartments as there are active substances (inhibitors and stimulators) which it is wished or which it is desirable to use.

The compositions according to the invention, or the kits according to the invention, or the implementation of the process according to the invention, may also make use of various conventional additives which are used in the above fields, in particular cosmetic additives in the case of topical applications (skin care products in particular), and chosen for example from UV screening agents, thickening agents, penetration agents such as urea and alpha-hydroxy acids, organic solvents such as ethanol, isopropanol and alkylene glycols, surface active agents chosen from non-ionic surfactants such as alkylpolyglycosides, cationic surfactants, anionic surfactants and amphoteric surfactants, dissolving agents, emollients, dyes, perfumes, preserving agents and, in general, all the excipients usually encountered in the field of the Pharmacopoeia.

It is also possible to incorporate into the compositions according to the invention, conventional compounds in the field of combating adiposity and/or slimming, for example certain plant extracts of oily, water-soluble or aqueous-alcoholic type. Among these, there may more particularly be mentioned the extract of English ivy (Hedera Helix), of arnica (Arnica Montana L), of rosemary (Rosmarinus officinalis N), of calendula (Calendula officinalis), of sage (Salvia officinalis L), of ginseng (Panax ginseng), of St.-John's-Wort (Byperycum Perforatum), of butcher's-broom (Ruscus aculeatus L), of European meadowsweet (Filipendula ulmaria L), of big-flowered Jarva tea (Orthosiphon Stamincus Benth), of algae (Fucus Vesiculosus), of birch (Betula alba) and of cola nuts (Cola Nipida), it being possible, of course, for all of these extracts to be taken as mixtures.

The amounts of inhibitors present in the compositions according to the invention are not critical and may thus vary within very wide ranges, which depend in particular on the mode of presentation and/or of administration chosen for the compositions. It is possible in particular, to use the products pure. In the case, for example, of preparations for topical use, this amount may thus range with no problem from 0.0001% by weight to 100% by weight relative to the whole composition, preferably between 0.5% and 10% by weight. In the case of preparations intended for administration via a systemic route, the doses must remain compatible with the standard requirements associated with the toxicology and the presentation of the pharmaceutical products; in this regard, administration doses of between 1 µg/10 Kg (of the weight of the subject treated)/day and 15 g/10 Kg/day are generally suitable, preferably from 10 mg to 8 g/10 Kg/day.

In order to obtain appreciable effects, the frequency of administration of the composition, which may be variable depending on the amount of inhibitory agent used in each operation. Typically the amount of agent is adjusted to a concentration for application one to two times per day. The treatment is subsequently followed regularly, for several days, preferably for several weeks or even for several months. There is no drawback or contraindication in applying to the body the treatment according to the invention continually and daily. In the case of an administration via the topical route, application of the compositions is advantageously accompanied by simultaneous massaging of the treated part of the body.

It has been noted that sufficiently effective amounts of inhibitory agents used in the context of the present invention may generally remain very low.

The treatment may be of a patient in need of a reduction in the amount of fat stored in the patients' adipocytes (i.e. therapeutic administration), or may be administered to a patient who is trying to prevent the build up of fat in the patient's adipocytes (i.e. non-therapeutic administration).

The present invention is particularly useful in the field of cosmetic treatments aimed at obtaining local or generalized effects of slimming and/or thinning of the skin or of the figure (hips, buttocks, thighs, midriff and others) or in the field of treatments of various pathologies which are associated with adiposity, in particular obesity.

One of the great advantages of the present invention resides in the possibility of being able, as and when necessary or desirable, to perform "mild", very localized and selective treatments by virtue of the mode of application via the topical route.

The present invention may, of course, be applied both to human and to animal bodies.

However, other characteristics, aspects, aims and advantages of the invention will emerge even more clearly on reading the description which will follow, as well as on reading the various concrete, but in no way limiting, example intended to illustrate it. Concrete examples illustrating the invention will now be given.

EXAMPLE 1

The aim of this example is to demonstrate the effect in vitro of certain substances on glucose transport in the adipocytes.

The substances tested were as follows:
serine (G1)
threonine (G2)
bifidus powder (G3)
rutine (G4)
N-oleyldihydrosphingosine (G5)
D-sphingosine (G6)

1. Experimental procedure 1.1. Uptake of 2-deoxyglucose: the set of operations takes place at 37° C. Pre-adipocyte cells (line Ob17) are differentiated by culture in a medium containing 8% of bovine serum, 17 nM of insulin, 2 nM of triiodothyronine and 2 nM of somatotropin (differentiation medium). Once differentiated, the cells, which are and which remain attached to the bottom of the culture dish (16 mm well), are maintained in the presence of 1 ml of DME medium supplemented with 8% of calf foetal serum, in the absence or in the presence of 100 nM of insulin, and in the absence or in the presence of the above substances G1 to G6 at various concentrations. After 48 hours, the medium is removed and the same operation is repeated for 48 h. Chronic exposure to the substances G1-G6 thus lasts for a total of 4 days.

The cells are subsequently washed for 1 h 30 with DME medium and are pre-incubated for 30 min in 1 ml of buffer at pH 7.4 containing 20 mM Hepes, 140 mM NaCl, 1 mM $CaCl_2$, 5 mM KCl, 2.5 MM $MgSO_4$ and 2% BSA-fatty acid poor (KRP/BSA buffer).

At time zero, 10 µl of [$^3$H]2-deoxyglucose (2-DOG) (0.1 mM final; 1 µCi/vial) are added. Each point in the kinetics (0–5–15 min) is performed in triplicate (3 separate wells per point). The reaction is stopped by three quick washes with "phosphate-buffered saline" (PBS) pH 7.4 at 4° C. containing 0.1 mM non-radioactive DOG. The cells are subsequently lysed in 1 ml of 0.1N sodium hydroxide. A 0.9 ml aliquot is taken in order to measure the radioactivity incorporated and 0.1 ml is used for protein assay. The results are expressed as a mean ±SEM (pmoles of 2-DOG incorporated/min/mg of protein).

1.2—Viability: Trypan Blue exclusion technique and release of lactate dehydrogenase.

1.3—protein synthesis: The cells are treated as described in point 1.1 above and incubated at 37° C. in the presence of 1 ml of KRP buffer containing [$^3$H]leucine (10 µM final; 0.5 µCi per well). After 2 min, the reaction is stopped by washing with KRP buffer containing 10 µM non-radioactive leucine. The radioactivity of the cells is measured and the results are expressed as pmoles/min/mg protein (mean ±SEM). The values for the control cells, as for the cells treated chronically with the molecules G1 to G6, remained virtually identical (40±4 pmol/min/mg protein).

2. Results

The "basal" transport is that observed in differentiated cells maintained for 4 days in the absence of insulin and with increasing concentrations of the various substances G1 to G6.

The "insulin-stimulated" transport is that observed in differentiated cells maintained for 4 days in the presence of 100 nM insulin and with increasing concentrations of the various substances G1 to G6.

The results show that the uptake of 2-DOG is very significantly increased in the cells exposed chronically (4 days) to insulin. As expected, the transport is totally inhibited by 10 µM cytochalasin B, whether or not the cells had been exposed to insulin.

Moreover, the results show that the "insulin-stimulated" transport is only marginally decreased by chronic exposure to the various substances G1 to G6, whereas the "basal" transport decreases significantly by chronic exposure to 10 µg/ml of the substances G1 (−30%), G4 (−30%) and G5 (−35%).

3—Conclusions

The various substances G1 to G6 exhibit no cytotoxic nature at the concentrations used. The inhibitory effect is observed for certain given (G1, G4 and G5) as being chronic on the transport of 2-DOG into cells which have not undergone a treatment with insulin; in contrast, the substances G2 (similar to G1), G3 and G6 (similar to G5) give no appreciable effect. The chronic effects of the specific substances G1, G4 and G5 on decreasing the transport of 2-DOG into cells not exposed to insulin quite probably take priority due to an effect on GLUT-4 and due to an absence of effect on GLUT-1; without wishing to limit the present invention to any particular theory, this effect on GLUT-4 could then be produced either by decreasing the synthesis of this transporter or by decreasing the proportion of GLUT-4 present at the cell surface without modifying their synthesis.

EXAMPLE 2

The aim of this example is to illustrate various concrete formulations, of cosmetic type, falling within the scope of the present invention.

A) Balm (topical route):

| | |
|---|---|
| Ozokerite | 10 g |
| Isopropyl palmitate | 10 g |
| White vaseline | 15 g |
| Preserving agent | 0.2 g |
| Antioxidants | 0.3 g |
| Perfume | 1 g |
| N-oleyldihydrosphingosine | 1 g |
| Liquid paraffin qs | 100 g |

B) Balm (topical route):

| | |
|---|---|
| Ozokerite | 20 g |
| Liquid purcellin oil | 10 g |
| White vaseline | 15 g |
| Preserving agent | 0.2 g |
| Antioxidant | 0.3 g |
| N-oleyldihydrosphingosine | 1 g |
| α-Tocopherol nicotinate | 0.1 g |
| Liquid paraffin qs | 100 g |

C) Emulsified gel of O/W type (topical route):

| | |
|---|---|
| Carbopol ® 940 (marketed by Goodrich) | 0.6 g |
| Volatile silicone oil | 3 g |
| Purcellin oil | 7 g |
| Tefose ® 63 | 3 g |
| Preserving agent | 0.3 g |
| Ethyl alcohol | 15 g |
| Perfume | 0.4 g |
| Triethanolamine | 0.2 g |
| Rutine | 0.2 g |
| Caffeine | 3 g |
| Demineralized water qs | 100 g |

D) Aqueous-alcoholic gel (topical route):

| | |
|---|---|
| Carbopol ® 941 (marketed by Goodrich) | 1 g |
| Triethanolamine | 1 g |
| 95% Ethanol | 60 g |
| Glycerol | 3 g |
| Propylene glycol | 2 g |
| Serine | 0.3 g |
| Aescin | 0.5 g |
| Demineralized water qs | 100 g |

E) Anhydrous gel (topical route):

| | |
|---|---|
| Absolute ethanol | 61 g |
| Hydroxyethyl cellulose | 0.8 g |
| Propylene glycol | 25 g |
| Polyethylene glycol | 12 g |
| N-Oleyldihydrosphingosine | 0.2 g |

F) Emulsion of O/W type (topical route):

| | |
|---|---|
| Volatile silicone oil | 10 g |
| Perhydrosqualene | 18 g |
| Liquid paraffin | 5 g |
| Liquid lanolin | 4 g |
| Arlacel ® 165 (marketed by Atlas) | 6 g |
| Tween ® 60 (marketed by Atlas) | 2 g |
| Cetyl alcohol | 1.2 g |
| Stearic acid | 2.5 g |
| Triethanolamine | 0.1 g |
| Preserving agent | 0.3 g |
| Antioxidants | 0.3 g |
| Rutine | 1 g |
| Lactic acid | 0.5 g |
| Demineralized water qs | 100 g |

G) Emulsion of O/W type (topical route):

| | |
|---|---|
| Propylene glycol | 2 g |
| PEG 400 | 3 g |
| Preserving agent | 0.3 g |
| Carbopol ® 941 | 0.2 g |
| Isopropyl myristate | 1 g |
| Cetyl alcohol | 3 g |
| Stearic acid | 3 g |
| Glycerol monostearate | 3 g |
| Corn oil | 2 g |
| Perfume | 0.5 g |
| Serine | 0.2 g |
| Demineralized water qs | 100 g |

H) Clear gel (topical route)

| | |
|---|---|
| Oxyethylenated nonylphenol (containing 12 mol of ethylene oxide) | 5 g |
| Carbopol ® 940 | 1 g |
| Ethyl alcohol | 30 g |
| Triethanolamine | 0.3 g |
| Glycerine | 3 g |
| Perfume | 0.3 g |
| Preserving agent | 0.3 g |
| Serine | 0.5 g |
| Demineralized water qs | 100 g |

I) Cream containing liposomes (topical route):

| | |
|---|---|
| Polyglycerolated cetyl alcohol | 3.8 g |
| B-sitosterol | 3.8 g |
| Dicetyl phosphate | 0.4 g |
| Preserving agent | 0.3 g |
| Sunflower oil | 35 g |
| Perfume | 0.6 g |
| Carbopol ® 940 | 0.2 g |
| Triethanolamine | 0.2 g |
| N-oleyldihydrosphingosine | 0.05 g |
| Serine | 0.5 g |
| Caffeine | 1 g |
| Demineralized water qs | 100 g |

J) Gelatine capsules (oral route):

| | |
|---|---|
| Aerosil ® 200 (silica) | 5 g |
| Zinc stearate | 5 mg |
| Talc | 5 mg |
| Serine | 200 mg |
| Lactose qs | 400 mg |

All the formulations A)–I) above, after repeated application to skin, allowed an appreciable slimming effect to be obtained in individuals suffering from local adiposity. The same effect was observed after repeated administration of composition J) via the oral route.

This application is based on French Patent Application 93/14156, filed with the French Patent Office on Nov. 26, 1993, the entire contents of which are hereby incorporated by reference.

What is claimed as new and desired to be secured by Letters Patent of the United States is:

1. A process for combating adiposity by obtaining a localized effect of slimming, comprising topically administering to the site of the body in need thereof, an amount effective for the inhibition of glucose uptake of at least one glucose-uptake inhibitor which does not contain the element of sulfur and capable of limiting or inhibiting the uptake of glucose by adipocytes, selected from the group consisting of rutine, N-oleyldihydrosphingosine and mixture thereof; and caffeine in an amount effective for stimulating lipolysis.

2. The process of claim 1, wherein said caffeine is co-administered with said glucose-uptake inhibitor.

3. The process of claim 1, wherein said caffeine is administered separately from said glucose-uptake inhibitor.

4. The process of claim 1, wherein said at least one glucose-uptake inhibitor is N-oleyldihydrosphingosine.

* * * * *